US012583827B2

(12) United States Patent
Ernst et al.

(10) Patent No.: US 12,583,827 B2
(45) Date of Patent: Mar. 24, 2026

(54) PRODUCTS OBTAINED BY THE CONVERSION OF GLYCOLALDEHYDE DERIVATIVES AND AMINATING AGENTS AND THEIR CONVERSION TO ETHYLENEAMINES AND ETHANOLAMINES

(71) Applicant: BASF SE, Ludwigshafen am Rhein (DE)

(72) Inventors: Martin Ernst, Ludwigshafen am Rhein (DE); Tatjana Huber, Ludwigshafen am Rhein (DE); Johann-Peter Melder, Ludwigshafen am Rhein (DE); Stephanie Jaegli, Ludwigshafen am Rhein (DE); Thomas Krug, Ludwigshafen am Rhein (DE)

(73) Assignee: BASF SE, Ludwigshafen am Rhein (DE)

( * ) Notice: Subject to any disclaimer, the term of this patent is extended or adjusted under 35 U.S.C. 154(b) by 1031 days.

(21) Appl. No.: 17/617,205

(22) PCT Filed: Jun. 2, 2020

(86) PCT No.: PCT/EP2020/065201
§ 371 (c)(1),
(2) Date: Dec. 7, 2021

(87) PCT Pub. No.: WO2020/249428
PCT Pub. Date: Dec. 17, 2020

(65) Prior Publication Data

US 2022/0235015 A1 Jul. 28, 2022

(30) Foreign Application Priority Data

Jun. 11, 2019 (EP) .................................... 19179444
Jun. 11, 2019 (EP) .................................... 19179445
Jun. 11, 2019 (EP) .................................... 19179449

(51) Int. Cl.

| | |
|---|---|
| ***C07D 251/04*** | (2006.01) |
| ***C07C 29/154*** | (2006.01) |
| ***C07C 209/16*** | (2006.01) |
| ***C07C 209/26*** | (2006.01) |
| ***C07C 209/62*** | (2006.01) |
| ***C07C 209/84*** | (2006.01) |
| ***C07C 213/02*** | (2006.01) |
| ***C07C 213/04*** | (2006.01) |
| ***C07C 213/08*** | (2006.01) |
| ***C07C 213/10*** | (2006.01) |

(52) U.S. Cl.

CPC .......... *C07D 251/04* (2013.01); *C07C 29/154* (2013.01); *C07C 209/16* (2013.01); *C07C 209/26* (2013.01); *C07C 209/62* (2013.01); *C07C 209/84* (2013.01); *C07C 213/02* (2013.01); *C07C 213/04* (2013.01); *C07C 213/08* (2013.01); *C07C 213/10* (2013.01)

(58) Field of Classification Search

CPC .................................................. C07D 251/04
USPC ........................................................ 544/216
See application file for complete search history.

(56) References Cited

U.S. PATENT DOCUMENTS

| | | | |
|---|---|---|---|
| 4,322,568 | A | 3/1982 | Weiss |
| 4,503,260 | A | 3/1985 | Auvil et al. |
| 4,677,213 | A | 6/1987 | Kitagawa et al. |
| 6,147,261 | A | 11/2000 | Knifton et al. |
| 6,534,441 | B1 | 3/2003 | Bartley et al. |
| 7,750,189 | B2 | 7/2010 | Kubanek et al. |
| 2004/0022912 | A1 | 2/2004 | Majerski et al. |
| 2007/0249871 | A1 | 10/2007 | Almeida Lenero et al. |

(Continued)

FOREIGN PATENT DOCUMENTS

| | | | |
|---|---|---|---|
| CN | 107011194 | A | 8/2017 |
| DE | 4400591 | A1 | 7/1995 |

(Continued)

OTHER PUBLICATIONS

International Search Report and Written Opinion received for PCT Patent Application No. PCT/EP2020/065201, mailed on Sep. 4, 2020, 7 pages.
European Search Report for EP Patent Application No. 19179444.5, Issued on Nov. 25, 2019, 2 pages.
European Search Report for EP Patent Application No. 19179445.2, Issued on Dec. 16, 2019, 3 pages.
European Search Report for EP Patent Application No. 19179449.4, Issued on Dec. 3, 2019, 3 pages.
International Preliminary Report on Patentability received for PCT Patent Application No. PCT/EP2020/065201, mailed on Dec. 23, 2021, 7 pages.

(Continued)

*Primary Examiner* — Taofiq A Solola
(74) *Attorney, Agent, or Firm* — Faegre Drinker Biddle & Reath LLP

(57) ABSTRACT

A process for the manufacture of ethyleneamines and ethanolamines, comprising the steps of (i) converting a glycolaldehyde derivative of formula (II), in which $R^2$, $R^3$ are—the same or different—hydrogen, alkyl, such as $C_{1-6}$-alkyl, or cycloalkyl such as Cs-e-cycloalkyl; and an animating agent of formula (III); in which R1 is hydrogen (H), alkyl, such as $C_{1-6}$-alkyl, or cycloalkyl such as $C_{3-6}$-cycloalkyl, in the gas or liquid phase; (ii) feeding the reaction products obtained in step (i) into a hydrogenation reactor, where the reaction products are converted with hydrogen in the presence of a hydrogenation catalyst.

(II)

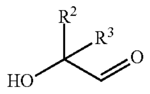

(III)

$R^1-NH_2$

18 Claims, No Drawings

(56) References Cited

U.S. PATENT DOCUMENTS

| | | | |
|---|---|---|---|
| 2008/0081931 | A1 | 4/2008 | Puckette et al. |
| 2009/0012333 | A1 | 1/2009 | Almeida Lenero et al. |

FOREIGN PATENT DOCUMENTS

| | | | |
|---|---|---|---|
| EP | 1697291 | A1 | 9/2006 |
| JP | 03-246248 | A | 11/1991 |
| JP | 03-279342 | A | 12/1991 |
| WO | 2005/058788 | A1 | 6/2005 |
| WO | 2011/082967 | A1 | 7/2011 |
| WO | 2011/082994 | A1 | 7/2011 |
| WO | 2020/028262 | * | 2/2020 |

OTHER PUBLICATIONS

Liang et al., "Production of Primary Amines by Reductive Amination of Biomass-Derived Aldehydes/Ketones", Angew. Chemie International Edition, Jan. 1, 2017, pp. 3050-3054.

Liang, et al., "Production of Primary Amines by Reductive Amination of Biomass-Derived Aldehydes/Ketones", Angewandte Chemie, vol. 129, Issue 11, Mar. 6, 2017, pp. 3096-3100.

Mohan, et al., "Pyrolysis of Wood/Biomass for Bio-oil:? A Critical Review", Energy & Fuels, vol. 20, Issue 3, Mar. 10, 2006, pp. 848-889.

Pelckmans, et al., "Catalytic Reductive Aminolysis of Reducing Sugars: Elucidation of Reaction Mechanism", ACS Catalysis, vol. 8, Issue 5, 2018, pp. 4201-4212.

Vitasari et al.,, "Extraction of bio-based glycolaldehyde from wood-derived pyrolysis oils", Eindhoven University of Technology, 2012, 149 pages.

* cited by examiner

PRODUCTS OBTAINED BY THE CONVERSION OF GLYCOLALDEHYDE DERIVATIVES AND AMINATING AGENTS AND THEIR CONVERSION TO ETHYLENEAMINES AND ETHANOLAMINES

CROSS-REFERENCE TO RELATED APPLICATIONS

This application is a national stage application (under 35 U.S.C. § 371) of PCT/EP2020/065201, filed Jun. 2, 2020, which claims benefit of European Application Nos. 19179444.5, 19179445.2, and 19179449.4, all filed Jun. 11, 2019, all four of which are incorporated herein by reference in their entirety.

The present invention relates to processes for the manufacture of ethyleneamines and ethanolamines by hydrogenation of intermediates formed by the conversion of an aminating agent and a glycolaldehyde derivative. The present invention further relates to a novel triazinane derivative, which is formed as an intermediate by the conversion of an aminating agent and a glycolaldehyde derivative.

Glycolaldehyde appears to be a useful raw material for the production of ethyleneamines and ethanolamines.

U.S. Pat. No. 6,534,441 describes a process for reductive amination of lower aliphatic alkane derivatives using a nickel/rhenium catalyst. A possible feedstock mentioned in the description is glycolaldehyde.

German patent application DE-A1-4400591 describes a process for preparing amino alcohols by reacting hydroxy carbonyl compounds with hydrogen and an aminating agent at temperatures of 0 to 300° C. and pressures of 1 to 400 bar over a catalyst which comprises 50 to 100% by weight of ruthenium. Glycolaldehyde is disclosed as suitable hydroxy carbonyl compound which can be employed in the process.

The conversion of hydroxy alkanals to diamines in the presence of ammonia and hydrogen in the presence of catalysts which comprise nickel or cobalt is disclosed in U.S. Pat. No. 6,147,261. U.S. Pat. No. 6,147,261 teaches that hydroxy alkanals are very reactive and tends to oligomerization and polymerization.

Although U.S. Pat. No. 6,147,261, DE-A1-4400591 and U.S. Pat. No. 6,534,441 mention the use of glycolaldehyde as a feedstock in a reaction with an aminating agent, the specific reaction demonstrated by examples has not been described.

CN107011194 discloses a method for conversion of glycolaldehyde with different aminating agents, such as ammonia, methylamine, ethylamine and butylamine in the presence of hydrogen using noble metal catalysts which comprised rare earth metals.

The conversion of glycolaldehyde with aminating agents, such as ammonia, in the presence of hydrogen was disclosed in WO2011/082994. Due to glycolaldehyde's tendency to form oligomers, such as the dimer 2,5-dihydroxy-1,4-dioxane, a six-membered ring compound formed having a high thermodynamic stability, the conversion required the pre-activation of non-noble metal amination catalysts to achieve high conversions.

The effect of catalyst pre-activation was later confirmed by Liang et al. (Angew. Chem. 2017, 129, 3096-3100) who studied the conversion of glycolaldehyde with ammonia in the presence hydrogen and Ru-catalysts.

Pelckmans et. Al (ACS Catal. 2018, 8, 4201-4212) studied the reductive amination of various sugars with dimethylamine in the presence of hydrogen and different metal catalysts. It was proposed that glycolaldehyde is formed as an intermediate during the reductive aminolysis of sugars. The authors therefore studied the reaction behavior of pure glycolaldehyde with dimethylamine and hydrogen over a nickel catalyst as a model reaction. High conversions to TMEDA and DMEOA were obtained in MeOH-solutions.

WO2011/082967 discloses the amination of glycolaldehyde with the aminating agents MEA and DEA in the presence of hydrogen and amination catalysts to yield alkanolamines.

The aforementioned applications disclose the conversion of glycolaldehyde in the presence of a heterogeneous catalyst, i.e. an amination or a hydrogenation catalyst.

The reaction of glycolaldehyde and primary amines as aminating agents in the absence of a heterogeneous catalyst is disclosed in U.S. Pat. No. 4,677,213. At temperatures from 0 to 70° C. under inert gas 2,5-diamino-1,4-dioxane derivatives are obtained. U.S. Pat. No. 4,677,213 discloses the further conversion of the dioxane derivatives with hydrocyanic acid to obtain amino acids.

The object of the present invention was to provide a process for the manufacture of ethyleneamines and ethanolamines which give high yields based on the glycolaldehyde used in the reaction. It was a further object to obtain high degrees of conversion of glycolaldehyde and to obtain the desired ethyleneamines and ethanolamines with a high selectivity. It was a further object to provide a process for the conversion of glycolaldehyde which does not require the pre-activation of catalysts as described in WO2011/082994.

The object of the present invention was achieved by a a process for the manufacture of ethyleneamines and ethanolamines, comprising the steps of (i) converting a glycolaldehyde derivative of formula (II)

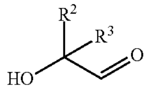

(II)

in which $R^2$, $R^3$ are—the same or different—hydrogen, alkyl, such as $C_{1-6}$-alkyl, or cycloalkyl such as $C_{3-6}$-cycloalkyl; and an aminating agent of formula (III);

$$R1\text{-}NH_2 \quad \text{(III)}$$

in which $R^1$ is hydrogen (H), alkyl, such as $C_{1-6}$-alkyl, or cycloalkyl such as $C_{3-6}$-cycloalkyl, in the gas or liquid phase;

(ii) feeding the reaction products obtained in step (i) into a hydrogenation reactor, where the reaction products are converted with hydrogen in the presence of a hydrogenation catalyst.

Step (i):

In the process of the present invention a glycolaldehyde derivative of formula (II) is converted with an aminating agent of formula (III).

In the glycolaldehyde derivative of formula (II), the residues $R^2$ and $R^3$ may be Hydrogen (H), alkyl, such as $C_{1-6}$-alkyl, preferably $C_{1-4}$-alkyl, in particularly methyl, ethyl, n-propyl, iso-propyl, n-butyl, sec-butyl, tert-butyl and iso-butyl.

Cycloalkyl, such as $C_{3-6}$-cycloalkyl, preferably cyclopropyl, cyclobutyl, cyclopentyl and cyclohexyl.

In formula (II), the residues $R^2$ and $R^3$ may be the same or different.

It is possible to use mixtures of different glycolaldehyde derivatives of formula (II) having different residues $R^2$ and $R^3$.

Preferably, the glycolaldehyde derivative of formula (II) is glycolaldehyde, with $R^2$ and $R^3$ both being hydrogen residues (H).

Glycolaldehyde is commercially available and can be prepared, for example, by oxidizing ethylene glycol (see, for example, JP 3246248 and JP 3279342).

Glycolaldehyde is preferably synthesized by reaction of formaldehyde with carbon monoxide and hydrogen, as described, for example, in US 2009012333, US 2008081931, US 2007249871, EP 1697291, U.S. Pat. Nos. 4,503,260 and 4,322,568.

Glycolaldehyde can also be obtained from the cracking of biomass, such as sugars or wood, as disclosed in US 2004/0022912 or by D. Mohan et al. ("Pyrolysis of Wood/Biomass for Bio-Oil", Energy Fuels 2006, 20, 3, 848-889) or by C. R. Vitasari (Extraction of bio-based glycolaldehyde from wood-derived pyrolysis oils Eindhoven: Technische Universiteit Eindhoven DOI: 10.6100/IR738958).

In the aminating agent of formula (III), the residue $R^3$ may be

Hydrogen (H), alkyl, such as $C_{1-6}$-alkyl, preferably $C_{1-4}$-alkyl, in particularly methyl, ethyl, n-propyl, iso-propyl, n-butyl, sec-butyl, tert-butyl and iso-butyl.

Cycloalkyl, such as $C_{3-6}$-cycloalkyl, preferably cyclopropyl, cyclobutyl, cyclopentyl and cyclohexyl.

Preferably the aminating agent of formula (III) is methylamine, ethylamine, n-propyl-amine, iso-propyl amine, n-butylamine, sec-butylamine, tert-butylamine and iso-butylamine.

Most preferably the aminating agent of formula (III) is ammonia.

It is also possible to use mixtures of aminating agents of formula (III).

The aminating agent and the glycolaldehyde derivative can be provided to step (i) in the gas or liquid form.

In a preferred embodiment, the glycolaldehyde is provided to step (i) in the liquid form. Some glycolaldehyde derivatives of formula (II) are liquid at ambient temperatures. Glycolaldehyde itself has a melting point of about 96-97° C. and a boiling point of about 131° C.

Due to the tendency of glycolaldehyde to form stable dimers in the solid and liquid phase, in a preferred embodiment the glycolaldehyde derivatives are provided to step (i) in the liquid form as a mixture in one or more solvents.

The solvent may be any solvent which is inert under the reaction conditions and has a sufficient solubility for the reactants.

Preferably the one or more solvents are selected from the group consisting of water, alcohols, non-cyclic or cyclic ethers, polyalkylethers and alkoxypolyalkylethers.

More preferably the one or more solvents are selected from the group consisting of water, methanol, ethanol, methyl tert-butyl ether, ethyl tert-butyl ether, dioxane, tetrahydrofuran, tetraethylene glycol dimethyl ether (tetraglyme), dipropylene glycol dimethyl ether (proglyme), bis(2-methoxyethyl) ether (diglyme) or other ethers of oligo- and polypropyleneoxides and oligo- and polyethyleneoxides or mixed oligo- or polyalkyleneoxides.

Particular preference is given to water, THF, tetraglyme, proglyme and diglyme.

Most preferably mixtures of water and tetrahydrofuran are used as solvents, wherein the molar ratio of water to THF is in the range of 1:1 to 20:1, more preferably 4:1 to 15:1 and most preferably 5:1 to 10:1.

Even more preferably mixtures of water and alkoxypolyalkylethers are used as solvents, wherein the molar ratio of water to the alkoxypolyalkylethers are in the range of 200:1 to 100:10, more preferably 150:1 to 100:5 and most preferably 125:1 to 100:3. Preferably, the alkoxypolyalkylethers are selected from the group consisting of proglyme, diglyme and tetraglyme.

Preferably the concentration of the solutions of the glycolaldehyde derivatives of formula (II) are in the range of 1 to 95 preferably 10 to 85, more preferably 25 to 80 and most preferably 50 to 75 percent by weight, based on the weight of the glycolaldehyde derivative of formula (II) and the total weight of the one or more solvents in which the glycolaldehyde derivative of formula (II) is dissolved.

In a further preferred embodiment, solutions of the glycolaldehyde derivative of formula (II) are obtained directly from a manufacturing process of the glycolaldehyde derivative of formula (II). Such solutions may be obtained from the cracking of aqueous solutions of organic feedstocks at high temperatures and condensing the gaseous effluent obtained from such cracking reactions.

In a more preferred embodiment, a glycolaldehyde solution is obtained by (i) the hydrous thermolysis of sugars, such as the process disclosed in US 2004/0022912, which is hereby incorporated by reference, and (ii) condensing the gaseous effluent from such a cracking process, or the processes described by D. Mohan et al. ("Pyrolysis of Wood/Biomass for Bio-Oil", Energy Fuels 2006, 20, 3, 848-889) or by C. R. Vitasari (Extraction of bio-based glycolaldehyde from wood-derived pyrolysis oils Eindhoven: Technische Universiteit Eindhoven DOI: 10.6100/IR738958), which are also incorporated herein by reference, in which glycolaldehyde is obtained by the pyrolysis of wood.

Preferably, the concentration of glycolaldehyde in such aqueous solutions is in the range of 5 to 80 percent by weight, most preferably 10 to 70 percent by weight and most preferably 25 to 60 percent by weight.

The aqueous solutions obtained by such processes may comprise other oxygenates, such as formaldehyde, hydroxyacetone (acetol), dihydroxyacetone, glyoxal, methylglyoxal (pyruvaldehye), acetic acid, levulinic acid, propionic acid, acrylic acid, glycolic acid, methanol, acetone and formic acid. One or more of the above listed solvents may be added to such aqueous glycolaldehyde solutions in amounts set out above before providing the aqueous solutions to step (i).

In a more preferred embodiment, the glycolaldehyde derivative is provided to step (i) in the gaseous form.

In one embodiment, the glycolaldehyde derivative is provided in the gaseous form by evaporation of the liquid glycolaldehyde derivate in its pure form.

In a more preferred embodiment, the glycolaldehyde derivative is provided in the gaseous form by evaporation of a solution of the glycolaldehyde derivative in one or more solvents. Evaporation from a solution is particularly preferred for those glycolaldehyde derivatives, which tend to form high boiling dimers, and which tend to oligomerize or polymerize upon heating.

Suitable solvents from which the glycolaldehyde derivative can be provided in the gaseous form are solvents which are inert under the reaction conditions and which have a sufficient solubility for the reactants.

Preferably the one or more solvents are selected from the group consisting of water, alcohols, non-cyclic or cyclic ethers, polyalkylethers and alkoxypolyalkylethers.

More preferably the one or more solvents are selected from the group consisting of water, methanol, ethanol, methyl tert-butyl ether, ethyl tert-butyl ether, dioxane, tetrahydrofuran, tetraethylene glycol dimethyl ether (tetraglyme), dipropylene glycol dimethyl ether (proglyme) or bis(2-methoxyethyl) ether (diglyme).

Most preferably mixtures of water and tetrahydrofuran are used as solvents, wherein the molar ratio of water to THF is in the range of 1:1 to 20:1, more preferably 4:1 to 15:1 and most preferably 5:1 to 10:1.

Even more preferably mixtures of water, THF and alkoxypolyalkylethers are used as solvents, wherein the molar ratio of water to the alkoxypolyalkylethers are in the range of 200:1 to 100:10, more preferably 150:1 to 100:5 and most preferably 125:1 to 100:3 and the ratio of water to THF is in the range described above. Preferably, the alkoxypolyalkylethers are selected from the group consisting of proglyme, diglyme and tetraglyme.

Preferably the concentration of the solutions of the glycolaldehyde derivatives of formula (II) from which the glycolaldehyde derivative is evaporated from are in the range of 1 to 80 preferably 2.5 to 50, more preferably 5 to 30 and most preferably 5 to 20 percent by weight, based on the weight of the glycolaldehyde derivative of formula (II) and the total weight of the one or more solvents in which the glycolaldehyde derivative of formula (II) is dissolved. The concentration of the solutions from which the glycolaldehyde derivative is evaporated from are usually lower than the concentration of the solutions used for the liquid phase reaction, because glycolaldehyde has a tendency to oligomerize and polymerize during the evaporation process.

Evaporation of the glycolaldehyde derivate of formula (II) or their respective solutions may be performed by operations well-known in the arts, e.g. by heating the liquids to temperatures above the boiling point of the glycolaldehyde derivative of formula (II) and/or by reducing the pressure and or by passing a stream of gas over the liquid glycolaldehyde derivative of formula (II).

Preferably, the glycolaldehyde derivative of formula (II) transferred into the gas phase by evaporation by heating in a stream of gas.

The gas is preferably hydrogen or an inert gas, such as nitrogen or a noble gas, such as He, Ne Ar, Kr or Xe.

Preferably, the gas is hydrogen, nitrogen or a mixture thereof.

Evaporators which can be used for the evaporation of the glycolaldehyde derivative and their respective solutions are natural or forced circulation evaporators, falling film evaporators, rising film (or long tube vertical) evaporators, climbing and falling-film plate evaporators, multi-effect evaporators, and agitated thin film evaporators. The evaporation can also be performed by a flash evaporation.

In a further preferred embodiment, the glycolaldehyde derivative of formula (II) in the gaseous form is directly provided by a manufacturing process in which the glycolaldehyde derivative of formula (II) is produced.

Such gaseous streams may be obtained from the cracking of aqueous solutions of organic feedstocks at high temperatures.

In a more preferred embodiment, a glycolaldehyde solution is obtained by the hydrous thermolysis of sugars, such as the process disclosed in US 2004/0022912, which is hereby incorporated by reference.

Using streams directly from production, in which the glycolaldehyde derivative exists already in the gaseous form has the advantage that the concentration of glycolaldehyde derivative in the gas stream can be higher compared to streams, in which the glycolaldehyde derivative in the gaseous form is obtained by evaporation from a solution of the glycolaldehyde derivative- Accordingly, the concentration of glycolaldehyde in such gaseous streams in this preferred embodiment is preferably in the range of 5 to 80 percent by weight, most preferably 10 to 70 percent by weight and most preferably 25 to 60 percent by weight.

The gaseous streams obtained by such processes may comprise other oxygenates, such as formaldehyde, hydroxyacetone (acetol), dihydroxyacetone, glyoxal, methylglyoxal (pyruvaldehyde), acetic acid, levulinic acid, propionic acid, acrylic acid, glycolic acid, methanol, acetone and formic acid.

The aminating agent of formula (III) may also be provided to step (i) in the gas or liquid form.

If the aminating agent is used in its liquid form, it is preferably used in its pure form.

The aminating agent may also be provided in form of its solution in one or more solvents. Preferably, the one or more solvents are the same as the solvents used for the preparation of the solutions of the glycolaldehyde derivative. More preferably, aqueous solutions of the aminating agent are being provided to step (i).

The concentration of the aminating agent in the solutions is preferably in the range of 5 to 75 percent by weight, more preferably 10 to 60 percent by weight and more preferably 15 to 35 percent by weight, based on the total weight of aminating agents and the sum of all solvents used for the solutions.

The aminating agent may also be provided in the gaseous form.

Some of the preferred aminating agents, such as ammonia, methylamine and ethylamine exist in a gaseous form under ambient conditions.

Alternatively, the aminating agents may be transferred to the gas phase by evaporation of the aminating agents in their pure form or by evaporation of the aforementioned solutions of the aminating agents.

The molar ratio of the glycolaldehyde derivative of formula (II) and the aminating agent is preferably in the range of 1:1 to 100:1, more preferably in the range of 1:1 to 25:1 and most preferably in the range of 1:1 to 15:1.

The conversion of the glycolaldehyde derivative and the aminating agent are preferably carried out under conditions in which hydrogenation or reductive amination of the glycolaldehyde derivative of formula (II), the aminating agent of formula (III) and any reaction products of the aminating agent and glycolaldehyde derivative, in particular any triazinane derivative of formula (I) and any diamino dioxane derivative of formula (IV), is substantially impeded or suppressed. In particular such conditions comprise the absence of a hydrogenation catalyst and/or hydrogen in step (i). If hydrogen is present in step (i), step (i) is preferably conducted in the absence of a hydrogenation catalyst. If a hydrogenation catalyst is present in step (i), step (i) is preferably conducted in the absence of hydrogen. If both hydrogen and a hydrogenation catalyst are present during step (i), the reaction condition described below—especially the temperature—is selected to be in a range in which hydrogenation is effectively suppressed, e.g. ambient temperatures. Hydrogenation and reductive amination are substantially impeded, if only minor amounts of ethyleneamines, such as ethylenediamine, and alkanolamines, such monoethanolamine and diethanolamine, are formed during step (i).

The conversion is preferably carried out under conditions as to substantially prevent the glycolaldehyde derivative from oxidation. It is thus preferred to that the reaction is carried out under inert conditions, preferably in a sealed system or more preferably under a stream of an inert gas, such as hydrogen, nitrogen or a noble gas, such as He, Ne Ar, Kr or Xe or mixtures thereof.

The conversion of the glycolaldehyde derivative and the aminating agent may be performed in the liquid phase.

The conversion of the glycolaldehyde derivative and the aminating agent may be performed continuously, batch-wise or semi-continuously.

The conversion may be carried out in one or a series of reactors suitable for liquid phase reactions.

Preference is given to tubular reactors, reactors with external or internal recirculation, plug flow reactors, spray reactors, reaction columns, and stirred tank reactors.

In a particularly preferred embodiment, the conversion is carried out in a tubular reactor.

In a further particularly preferred embodiment, the conversion is carried out in a stirred tank reactor The reactants may be mixed before entering the reactor (pre-mixing) or they may be mixed inside the reactor.

Mixing may occur by feeding the feed streams into a suitable reactor or a common pipe leading to a suitable reactor.

Mixing may be facilitated by using conventional equipment, such as pipes, nozzles, valves, static mixers, agitators, stirrers, flow-meters, pumps, carrier-gases and the like.

The conversion of the glycolaldehyde derivative and the aminating agent in the liquid phase is preferably carried out in the range −25 to 150° C., more preferably −10 to 100° C. and most preferably 0 to 75° C.

Conversion in the liquid phase is preferably performed under a pressure in the range of 0.5 to 100 bar, more preferably 0.8 to 50 and most preferably 1 to 20 bar.

Most preferably, the conversion in the liquid phase is conducted at a pressure of about 1 bar and at ambient temperatures, such as temperatures in the range of 0 to 30° C.

In a preferred embodiment, the conversion of the glycolaldehyde derivative and the aminating agent is carried out in the gas phase.

The conversion of the glycolaldehyde derivative and the aminating agent may be performed continuously, batchwise or semi-continuously.

The conversion may be carried out in one or a series of reactors suitable for gas phase reactions.

Preference is given to tubular reactors, reactor chambers, or reactors with external or internal recirculation. In a particularly preferred embodiment, the conversion is carried out in a tubular reactor or a reaction chamber.

The gaseous reactants may be mixed before entering the reactor (pre-mixing) or they may be mixed inside the reactor.

Mixing may occur by feeding the gaseous feed streams into a suitable reactor or a common pipe leading to a suitable reactor.

Mixing in the gas-phase may be facilitated by using conventional equipment, such as pipes, nozzles, valves, static mixers, flow-meters, pumps, carrier-gases and the like.

The conversion in the gas phase is preferably carried out in the range 50 to 300° C., more preferably 60 to 250° C. and most preferably 80 to 200° C.

Conversion in the gas phase is preferably performed under a pressure in the range of 0.1 to 200 bar, more preferably 0.5 to 100 bar, more preferably 1 to 30 bar and most preferably 1 to 20 bar.

The conversion of glycolaldehyde derivatives of formula (II) and aminating agents of formula (III) may lead to at least two different types of reaction products.

In U.S. Pat. No. 4,677,213 it has been disclosed that liquid phase conversion of a glycolaldehyde derivative and an aminating agent in step (i) results in reaction products which were identified as diamino dioxane derivatives of formula (IV)

(IV)

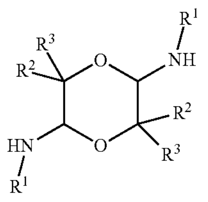

in which the residues $R^1$, $R^2$ and $R^3$ have the meaning given to them above.

In the formula (I) each $R^1$, each $R^2$ and each $R^3$ residue may be different. This may be the case if a mixture of different glycolaldehyde derivatives of formula (II) and a mixture of different aminating agents of formula (III) are used as starting materials.

However, more preferably, each $R^1$, each $R^2$ and each $R^3$ are the same

Most preferably, each $R^1$, each $R^2$ and each $R^3$ is hydrogen

Surprisingly, it has been found that the conversion of glycolaldehyde derivatives of formula (II) and aminating agents of formula (III) in the gas phase produces a triazinane derivative of formula (I)

(I)

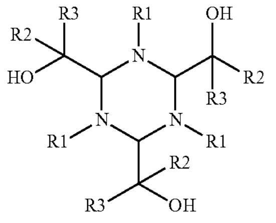

in which the residues $R^1$, $R^2$ and $R^3$ have the meaning given to them above.

Accordingly, the present invention is also directed to a triazinane derivative of formula (I).

In the formula (I) each $R^1$, each $R^2$ and each $R^3$ residue may be different. This may be the case if a mixture of different glycolaldehyde derivatives of formula (II) and a mixture of different aminating agents of formula (III) are used as starting materials.

However, more preferably, each $R^1$, each $R^2$ and each $R^3$ are the same

Most preferably, each $R^1$, each $R^2$ and each $R^3$ is hydrogen.

FIGS. 1 and 2 show the nuclear magnetic resonance spectrum ($^1$H-NMR and $^{13}$C-NMR) of the compound of formula (V)

(V)

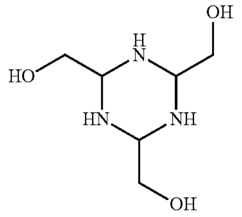 [SMILES: OCC1NC(CO)NC(CO)N1]

obtained from the reaction of glycolaldehyde with ammonia in the gas phase.

It cannot be excluded, that the liquid phase or the gas phase conversion of glycolaldehyde derivatives of formula (II) and aminating agents of formula (III) may lead to other structures than the diamino dioxanes or triazinanes referred to above. Accordingly, the reaction products of step (i) should not be limited to the specific structures disclosed above.

The reaction products obtained in a gas phase reaction by the conversion of the glycolaldehyde derivative of formula (II) and the aminating agent of formula (III) are usually high boiling products which tend to desublimate or condensate from the gas phase in solid or liquid form.

Separation of a solid or liquid from the gas phase can be carried out using conventional means, such as inertial separators (cyclone, settling chamber, vortex chamber) or wet separators (venturi scrubbers, jet scrubbers, scrubbing columns) using a scrubbing liquid.

Useful scrubbing liquid are liquids, in which the reaction product of the glycolaldehyde derivative and the aminating agent have a sufficient solubility.

Preferably the scrubbing liquids are selected from the group consisting of water, alcohols, non-cyclic or cyclic ethers, polyalkylethers and alkoxypolyalkylethers.

More preferably the one or more scrubbing liquids is selected from the group consisting of water, methanol, ethanol, methyl tert-butyl ether, ethyl tert-butyl ether, dioxane, tetrahydrofuran, tetraethylene glycol dimethyl ether (tetraglyme), dipropylene glycol dimethyl ether (proglyme) or bis(2-methoxyethyl) ether (diglyme).

Preferably, separation of the reaction products from the gas phase is carried out by condensation or desublimation of the reaction product. Condensation or desublimation is preferably carried out by feeding the gas stream to a heat exchanger.

Heat exchangers can be shell and tube heat exchangers or plate heat exchangers, preferably heat exchangers.

The heat exchangers used for the condensation or desublimation are preferably incorporated as a by-pass into the process and can thus be easily disconnected, cleaned and incorporated again, while the process is running.

The cleaning of the heat exchangers on the side facing the process stream is usually conducted with a scrubbing liquid which detaches the adhering by-products to achieve a cleaning effect. The by-products are preferably completely or partly dissolved and removed as solution or slurry from the heat exchanger. The speed of the cleaning by dissolution and discharge of the products is promoted by increasing the flow rate of the scrubbing liquid during the cleaning process or by scrubbing with a heated scrubbing liquid, to increase the solubility of the reaction products in the scrubbing liquid.

In a preferred embodiment, the conversion of the glycolaldehyde derivative and the aminating agent in step (i) is carried out in the presence of one or more scrubbing liquids. The scrubbing liquid is usually evaporated together with the aminating agent or the glycolaldehyde derivative and provided to step (i) in gaseous form. After conversion of the glycolaldehyde derivative and the aminating agent in step (i), the scrubbing liquids are also condensed at the heat exchangers. The condensation of the scrubbing liquid on the heat exchangers has the effect that any desublimated or condensed reaction products are intrinsically washed off from the heat exchangers.

Depending on the reaction conditions in step (i) and the solvents present during step (i), the reaction products obtained in a liquid phase reaction may be obtained as solutions in the one or more solvents present during step (i), or the reaction products obtained in a liquid phase reaction may at least partially precipitate from the liquid phase.

Separation of a solid from the liquid phase can be carried out using conventional means such as filtration, in particular cross-flow filtration, sedimentation or centrifugation. Prior to liquid-solid separation, the solutions may be concentrated by evaporating at least a part of the one or more solvents present during the reaction mixture or by cooling the solutions. Alternatively, solvent which is a precipitating agent for the reaction products may be added to facilitated liquid-solid separation. Preferably precipitating agents are nonpolar solvents, such as aliphatic hydrocarbons or aromatic hydrocarbons such as hexane, heptane, octane, cyclohexane, toluene or xylene.

Accordingly, the reaction products from the conversion of the glycolaldehyde derivative and the aminating agent in the gas or liquid phase may be obtained in a solid form or as dispersions or solutions in the one or more solvent present during the conversion and/or the scrubbing liquid used during work-up.

If the reaction products are obtained in step (i) as solutions or as dispersions of the reaction products in one or more solvent, the dispersions or the solutions may be directly fed into the hydrogenation step (ii).

In a preferred embodiment, the solutions or dispersions obtained from step (i) may be concentrated by evaporating at least part of the solvent comprised in such solutions to obtain a concentrated solution, a slurry or even a resinous solid. This embodiment has the advantage that solvents which have a lower hydrogen solubility can be at least partially removed and replaced against solvents having a higher hydrogen solubility.

If the reaction products are obtained in the solid form, it is preferred to dissolve the reaction products in one more solvent before feeding the reaction products into step (ii).

In a further preferred embodiment, (i) the solutions or dispersions of the reaction products, or
(ii) the separated reaction products, or
(iii) the concentrated solutions, slurry or resinous solids of the reaction products obtained after the concentration step can be compounded with one or more solvents.

Preferably the one or more solvents are selected from the group consisting of water, alcohols, non-cyclic or cyclic ethers, polyalkylethers and alkoxypolyalkylethers.

More preferably the one or more solvents are selected from the group consisting of water, methanol, ethanol, methyl tert-butyl ether, ethyl tert-butyl ether, dioxane, tetrahydrofuran, tetraethylene glycol dimethyl ether (tetraglyme), dipropylene glycol dimethyl ether (proglyme) or bis(2-methoxyethyl) ether (diglyme).

More preferably, the one or more solvent which is added has a higher hydrogen solubility than the solvent removed in the concentration step previously described.

Most preferably, water can be partially removed and replaced by methanol to yield mixtures of the reaction products in water and methanol.

It was found that the reaction products formed during step (i), especially the triazinane derivative of formula (I) and/or the diamino dioxane derivative of formula (iv) are useful as intermediates for the preparation of ethyleneamines and ethanolamines.

Step (ii):

According to the invention, the reaction products of the aminating agent and the glycolaldehyde derivate obtained in step (i) are fed into a hydrogenation reactor, where the reaction products from step (i) are converted with hydrogen in the presence of a hydrogenation catalyst.

The reaction products obtained from step (i) comprise diamino dioxane derivatives of formula (IV) and triazinane derivatives of formula (I). The reaction products obtained in step (i) may also comprise other adducts of the aminating agent and the glycolaldehyde derivative having a different structure than the triazinane or the diamino dioxane derivates.

In a preferred embodiment, the reaction products obtained in step (i) comprise 75 to 100 percent by weight, more preferably 80 to 100 percent by weight and most preferably 90 to 100 percent by weight of triazinane derivatives of formula (I).

In a further preferred embodiment, the reaction products obtained in step (i) comprise 75 to 100 percent by weight, more preferably 80 to 100 percent by weight and most preferably 90 to 100 percent by weight of diamino dioxane derivatives of formula (IV).

In a further preferred embodiment, the reaction products obtained in step (i) comprise 75 to 100 percent by weight, more preferably 80 to 100 percent by weight and most preferably 90 to 100 percent by weight of diamino dioxane derivatives of formula (IV) and triazinane derivatives of formula (I).

Accordingly, the present invention is also directed to a process for the manufacture of ethyleneamines and ethanolamines by converting a triazinane derivative of formula (I) and/or a diamino dioxane derivative of formula (IV) with hydrogen in a hydrogenation reactor in the presence of a hydrogenation catalyst.

Preferably, the reaction products obtained in step (i) are fed to the step (ii) in form of their solutions in one or more solvents.

Preferably the one or more solvents are water, ethers, preferably methyl tert-butyl ether, ethyl tert-butyl ether, dioxane or tetrahydrofuran (THF), and alcohols, preferably methanol, ethanol and iso-propanol.

Useful solvents also include suitable mixtures of the solvents listed above.

Particularly preferred solvents are methanol, THF, dioxane, glymes and water.

Particularly preferred solvents also include the reaction products of step (ii), such monethanolamine (MEOA), diethanolamine (DEOA), triethanolamine (TEOA) and ethylenediamine (EDA).

The concentration of the reaction products, which are fed to step (ii) in the one or more solvents is preferably in the range of 1 to 100 g reaction products per 100 g of solvents, more preferably 5 to 75 g reaction products per 100 g of solvents and most preferably 10 to 50 g reaction products per 100 g of solvents The hydrogenation step (ii) is carried out in the presence of hydrogen.

The hydrogen is generally used in technical grade purity. The hydrogen can also be used in the form of a hydrogen-comprising gas, i.e. with additions of other inert gases, such as nitrogen, helium, neon, argon or carbon dioxide. For example, hydrogen having a content of more than 99% by weight of hydrogen, preferably more than 99.9% by weight of hydrogen, more preferably more than 99.99% by weight of hydrogen, especially more than 99.999% by weight of hydrogen may be used in step (ii).

The partial pressure of hydrogen in step (ii) is preferably in the range of 2.5 to 200 bar, more preferably 5 to 150 bar and even more preferably 10 to 100 bar and most preferably 20 to 50 bar.

In a particularly preferred embodiment, the hydrogenation step (ii) is conducted in the presence of an acid. The presence of acids increases the yields of desired products, such as ethyleneamines and alkanolamines.

The acid can be any organic or inorganic acid.

Preference is given to organic carboxylic acids

Non-limiting examples of such organic carboxylic acids are:

saturated aliphatic monocarboxylic acids, such as formic, acetic, propionic, butyric, ethyl butyric, caproic, enanthic, caprylic, pelargonic, capric, undecanoic, lauric, myristic, palmitic, stearic, arachidic and the like, unsaturated aliphatic monocarboxylic acids, such as acrylic, methacrylic, crotonic, iso-crotonic, decylenic, palmitolic, oleic, linoleic and the like, saturated aliphatic dicarboxylic acids, such as oxalic, malonic, succinic, glutaric, adipic, pimelic, suberic, azelaic, sebacic and the like, unsaturated aliphatic dicarboxylic acids, such as maleic, fumaric, itaconic, citraconic, mesaconic acid and the like, aryl carboxylic acids, such as benzoic acid, napthoic acid, phthalic acid, isophthalic acid, terephthalic acid, naphthalic acid, pyromelletic acid, toluic acids, and acid esters of polycarboxylic acids such as alkyl acid phthalates and the like, hydroxy carboxylic acids, such as hydroxy acetic acid, hydroxy propionic acid, ethylidene lactic acid, hydroxy butyric acid, α-hydroxy isobutryric acid, hydroxy caproic acid, hydroxy stearic acid, tartronic acid, tartaric acid, malic acid, hydroxy benzoic acid and the like.

keto acids, such a pyruvic acid, oxoloacetic acid, levulinic acid

Preferred acids of the aforementioned groups comprise the monocarboxylic acids containing from 1 to 8 carbon atoms, in particular formic acid, acetic acid, propionic acid, butyric acid, valeric acid, caproic acid, enanthic acid, caprylic acid, pelargonic acid, capric acid dicarboxylic acids containing from 2 to 8 carbon atoms, in particular oxalic acid, maleic acid, succinic acid, glutaric acid, adipic acid, pimelic acid, suberic acid, azelaic acid, sebacic acid, hydroxy-carboxylic acids from 2 to 8 carbon atoms, in particular glycolic acid, lactic acid, citric acid and mandelic acid More preferably, the one or more organic carboxylic acids are selected from the group consisting of formic acid, acetic acid, lactic acid, glycolic acid, levulinic acid, acrylic acid and pyruvic acid.

The concentration of acids present during the hydrogenation step (ii) is preferably in the range of 0.1 to 25 percent by weight, more preferably 0.5 to 20 percent by weight and most preferably 1 to 10 percent by weight, based on the total weight of the feed stream fed into the hydrogenation step (ii).

In a further preferred embodiment, the hydrogenation step (ii) is conducted in the presence of ammonia.

Ammonia may already be present in the effluent stream coming from step (i).

Alternatively, additional ammonia may be added to step (ii).

Preferably the amount of ammonia present during the hydrogenation step (ii) is in the range of 1 to 50 percent by weight, preferably 5 to 40 percent by weight and more preferably 10 to 30 percent by weight, based on the total weight of the feed stream fed into the hydrogenations step.

The hydrogenation step (ii) is conducted in the presence of a hydrogenation catalyst.

The hydrogenation catalysts may in principle comprise nickel, cobalt, iron, copper, chromium, manganese, copper, molybdenum, tungsten and/or other metals of groups 8 and/or 9 and/or 10 and/or 11 of the periodic table of the elements Preference is given to using hydrogenation catalysts which comprise at least one metal selected from the group consisting of Cu, Co, Ni, Pd, Pt, Ru, Rh, Ag, Au, Re and Ir.

More preference is given to using hydrogenation catalysts which comprise at least one metal selected from the group consisting of Cu, Co, Ni, Pd, Pt and Ru.

The abovementioned catalysts can be doped in a customary manner with promoters, for example with chromium, iron, cobalt, manganese, molybdenum, titanium, tin, metals of the alkali metal group, metals of the alkaline earth metal group and/or phosphorus.

The hydrogenation catalyst can be a supported or unsupported catalyst.

Suitable support materials are carbon compounds such as graphite, carbon black and/or activated carbon, aluminum oxide (gamma, delta, theta, alpha, kappa, chi or mixtures thereof), silicon dioxide, zirconium dioxide, zeolites, aluminosilicates or mixtures thereof.

In a preferred embodiment of the invention, hydrogenation catalysts of the Raney type are being used.

As Raney catalysts, Raney cobalt catalysts, Raney nickel catalysts and/or Raney copper catalysts are preferably used. Raney cobalt catalysts are particularly preferred.

In a further preferred embodiment of the invention the hydrogenation catalysts are prepared by reduction of a catalyst precursor, in which the aforementioned metals are present in the form of oxygen comprising compounds, such as their oxides, carbonates or hydrogencarbonates.

The catalyst precursors can be prepared by known processes, for example by precipitation, precipitative application or impregnation.

In a preferred embodiment, catalyst precursors which are prepared by impregnating support materials are used in the process according to the invention (impregnated catalyst precursors).

The support materials used in the impregnation can, for example, be used in the form of powders or shaped bodies, such as extrudates, tablets, spheres or rings. Support material suitable for fluidized bed reactors is preferably obtained by spray drying.

Useful support materials include, for example, carbon such as graphite, carbon black and/or activated carbon, aluminum oxide (gamma, delta, theta, alpha, kappa, chi or mixtures thereof), silicon dioxide, zirconium dioxide, zeolites, aluminosilicates or mixtures thereof.

The abovementioned support materials can be impregnated by the customary methods (A. B. Stiles, Catalyst Manufacture—Laboratory and Commercial Preparations, Marcel Dekker, New York, 1983), for example by applying a metal salt solution in one or more impregnation stages. Useful metal salts generally include water-soluble metal salts, such as the nitrates, acetates or chlorides of the corresponding catalytically active components or the doping elements, such as cobalt nitrate or cobalt chloride. Thereafter, the impregnated support material is generally dried and optionally calcined.

The impregnation can also be performed by the so-called "incipient wetness method", in which the support material is moistened with the impregnating solution up to a maximum of saturation according to its water absorption capacity. However, the impregnation can also be performed in supernatant solution.

In the case of multistage impregnation processes, it is appropriate to dry and if appropriate to calcine between individual impregnation steps. Multistage impregnation can be employed advantageously when the support material is to be contacted with metal salts in a relatively large amount.

To apply a plurality of metal components to the support material, the impregnation can be performed simultaneously with all metal salts or in any desired sequence of the individual metal salts.

In a further preferred embodiment, catalyst precursors are prepared by means of a coprecipitation of all of their components. To this end, in general, a soluble compound of the corresponding active component and of the doping elements, and optionally a soluble compound of a support material is admixed with a precipitant in a liquid while heating and while stirring until the precipitation is complete.

The liquid used is generally water.

Useful soluble compounds of the active components typically include the corresponding metal salts, such as the nitrates, sulfates, acetates or chlorides of the aforementioned metals.

The soluble compounds of a support material used are generally water-soluble compounds of Ti, Al, Zr, Si etc., for example the water-soluble nitrates, sulfates, acetates or chlorides of these elements.

The soluble compounds of the doping elements used are generally water-soluble compounds of the doping elements, for example the water-soluble nitrates, sulfates, acetates or chlorides of these elements.

Catalyst precursors can also be prepared by precipitative application.

Precipitative application is understood to mean a preparation method in which a sparingly soluble or insoluble support material is suspended in a liquid and then soluble compounds, such as soluble metal salts, of the appropriate metal oxides, are added, which are then precipitated onto the suspended support by adding a precipitant (for example, described in EP-A2-1 106 600, page 4, and A. B. Stiles, Catalyst Manufacture, Marcel Dekker, Inc., 1983, page 15).

Useful sparingly soluble or insoluble support materials include, for example, carbon compounds such as graphite, carbon black and/or activated carbon, aluminum oxide (gamma, delta, theta, alpha, kappa, chi or mixtures thereof), silicon dioxide, zirconium dioxide, zeolites, aluminosilicates or mixtures thereof.

The support material is generally present in the form of powder or spall.

The liquid used, in which the support material is suspended, is typically water.

Useful soluble compounds include the aforementioned soluble compounds of the active components or of the doping elements.

Typically, in the precipitation reactions, the soluble compounds are precipitated as sparingly soluble or insoluble basic salts by adding a precipitant.

The precipitants used are preferably alkalis, especially mineral bases, such as alkali metal bases. Examples of precipitants are sodium carbonate, sodium hydroxide, potassium carbonate or potassium hydroxide.

The precipitants used may also be ammonium salts, for example ammonium halides, ammonium carbonate, ammonium hydroxide or ammonium carboxylates.

The precipitation reactions can be performed, for example, at temperatures of 20 to 100° C., preferably 30 to 90° C., especially at 50 to 70° C.

The precipitates formed in the precipitation reactions are generally chemically inhomogeneous and generally comprise mixtures of the oxides, oxide hydrates, hydroxides, carbonates and/or hydrogencarbonates of the metals used. It may be found to be favorable for the filterability of the precipitates when they are aged, i.e. when they are left alone for a certain time after the precipitation, if appropriate under hot conditions or while passing air through.

The precipitates obtained by these precipitation processes are typically processed by washing, drying, calcining and conditioning them.

After washing, the precipitates are generally dried at 80 to 200° C., preferably 100 to 150° C., and then calcined.

The calcination is performed generally at temperatures between 300 and 800° C., preferably 350 to 600° C., especially at 450 to 550° C.

After the calcination, the pulverulent catalyst precursors obtained by precipitation reactions are typically conditioned.

The conditioning can be affected, for example, by adjusting the precipitation catalyst to a particular particle size by grinding.

After the grinding, the catalyst precursor obtained by precipitation reactions can be mixed with shaping assistants such as graphite or stearic acid and processed further to shaped bodies. Common processes for shaping are described, for example, in Ullmann [Ullmann's Encyclopaedia Electronic Release 2000, chapter: "Catalysis and Catalysts", pages 28-32] and by Ertl et al. [Ertl, Knözinger, Weitkamp, Handbook of Heterogeneous Catalysis, VCH Weinheim, 1997, pages 98 ff].

As described in the references cited, the process for shaping can provide shaped bodies in any three-dimensional shape, for example round, angular, elongated or the like, for example in the form of extrudates, tablets, granules, spheres, cylinders or grains. Common processes for shaping are, for example, extrusion, tableting, i.e. mechanical pressing, or pelletizing, i.e. compacting by circular and/or rotating motions.

The conditioning or shaping is generally followed by a heat treatment. The temperatures in the heat treatment typically correspond to the temperatures in the calcination.

The catalyst precursors obtained by precipitation reactions comprise the catalytically active components in the form of a mixture of oxygen compounds thereof, i.e. especially as the oxides, mixed oxides and/or hydroxides. The catalyst precursors thus prepared can be stored as such.

The hydrogenation catalyst which is used in the process according to the invention is obtained by reducing catalyst precursors which have been prepared by impregnation or precipitation as described above after the calcination or conditioning.

The reduction of the dry, generally pulverulent catalyst precursor can be performed at elevated temperature in a moving or stationary reduction oven.

The reducing agent used is typically hydrogen or a hydrogen-comprising gas.

The hydrogen is generally used in technical grade purity. The hydrogen can also be used in the form of a hydrogen-comprising gas, i.e. in admixtures with other inert gases, such as nitrogen, helium, neon, argon or carbon dioxide. The hydrogen stream can also be recycled into the reduction as cycle gas, optionally mixed with fresh hydrogen and optionally after removing water by condensation.

The catalyst precursor is preferably reduced in a reactor in which the shaped catalyst bodies are arranged as a fixed bed. The catalyst precursor is more preferably reduced in the same reactor in which step (ii) is carried out.

In addition, the catalyst precursor can be reduced in a fluidized bed reactor in the fluidized bed. The catalyst precursor is generally reduced at reduction temperatures of 50 to 600° C., especially of 100 to 500° C., more preferably of 150 to 450° C.

The partial hydrogen pressure is generally from 1 to 300 bar, especially from 1 to 200 bar, more preferably from 1 to 100 bar, where the pressure figures here and hereinafter are based on the absolute measured pressure.

The duration of the reduction is preferably 1 to 20 hours and more preferably 5 to 15 hours.

During the reduction, a solvent can be supplied in order to remove water of reaction which forms and/or in order, for example, to be able to heat the reactor more rapidly and/or to be able to better remove the heat during the reduction. In this case, the solvent can also be supplied in supercritical form.

Suitable solvents used may be the above-described solvents. Preferred solvents are water; ethers such as methyl tert-butyl ether, ethyl tert-butyl ether, dioxane or tetrahydrofuran. Particular preference is given to water or tetrahydrofuran. Suitable solvents likewise include suitable mixtures.

The catalyst precursor can also be reduced in suspension, for example in a stirred autoclave. The temperatures are generally within a range from 50 to 300° C., especially from 100 to 250° C., more preferably from 120 to 200° C.

The reduction in suspension is generally performed at a partial hydrogen pressure of 1 to 300 bar, preferably from 10 to 250 bar, more preferably from 30 to 200 bar. Useful solvents include the aforementioned solvents.

The duration of the reduction in suspension is preferably 5 to 20 hours, more preferably 8 to 15 hours.

The catalyst can be handled under inert conditions after the reduction. The catalyst can preferably be handled and stored under an inert gas such as nitrogen, or under an inert liquid, for example an alcohol, water or the product of the particular reaction for which the catalyst is used. If appropriate, the catalyst must then be freed of the inert liquid before commencement of the actual reaction.

The storage of the catalyst under inert substances enables uncomplicated and safe handling and storage of the catalyst.

After the reduction, the catalyst can also be contacted with an oxygen-comprising gas stream such as air or a mixture of air with nitrogen. This affords a passivated catalyst. The passivated catalyst generally has a protective oxide layer. This protective oxide layer simplifies the handling and storage of the catalyst, such that, for example, the installation of the passivated catalyst into the reactor is simplified.

After passivation, the catalyst is usually activated. A catalyst can be activated by reducing a passivated catalyst. A passivated catalyst can be reduced as described above by treating the passivated catalyst with hydrogen or a hydrogen-comprising gas. The reduction conditions correspond generally to the reduction conditions employed in the reduction of the catalyst precursors. The activation generally eliminates the protective passivation layer.

An activated catalyst has to be handled under inert conditions during and after the activating reduction thereof.

The activated catalyst is preferably handled and stored under an inert gas, such as nitrogen, or under an inert liquid, for example an alcohol, water or the product of the particular reaction for which the catalyst is used. If appropriate, the activated catalyst then has to be freed of the inert liquid before commencement of the actual reaction.

Activation of the catalyst can also occur in situ during the hydrogenation step (ii).

In a preferred embodiment, the reaction products of step (i) are contacted with a reduced or activated hydrogenation catalyst.

Step (ii) is performed in a hydrogenation reactor.

The process according to the invention can be performed continuously, batchwise or semicontinuously.

Typical reactors are, for example, high-pressure stirred tank reactors, autoclaves, fixed bed reactors, fluidized bed reactors, moving beds, circulating fluidized beds, salt bath reactors, plate heat exchangers as reactors, staged reactors with a plurality of stages with or without heat exchange and removal/supply of substreams between the trays, in possible embodiments as radial flow or axial flow reactors, continuous stirred tanks, bubble reactors, etc., the reactor used in each case being that suitable for the desired reaction conditions (such as temperature, pressure and residence time).

The process according to the invention is preferably performed in a high-pressure stirred tank reactor, fixed bed reactor or fluidized bed reactor.

In a particularly preferred embodiment, the process according to the invention is performed in one or more fixed bed reactors.

In a further particularly preferred embodiment, the reaction products from step (i) are hydrogenated in a high-pressure stirred tank reactor.

The hydrogenation is typically performed at a pressure of 1 to 500 bar, preferably 10 to 350 bar, more preferably at a pressure of 50 to 300 bar and most preferably 80 to 220 bar. The pressure is maintained or controlled generally via the metered addition of the hydrogen.

The hydrogenation generally proceeds at temperatures of 15 to 350° C., preferably 50 to 250° C., more preferably 80 to 220° C.

The residence time in the hydrogenation step, in the case of performance in a batchwise process, is generally 15 minutes to 72 hours, preferably 60 minutes to 24 hours, more preferably 2 hours to 10 hours.

In the case of performance in a preferred continuous process, the catalyst hourly space velocity is generally in the range from 0.01 kg of reaction products obtained in step (i)/kg of catalyst/h to 3.0 kg of reaction products obtained in step (i)/kg of catalyst/h, preferably 0.05 kg of reaction products obtained in step (i)/kg of catalyst/h to 2.0 kg of reaction products obtained in step (i)/kg of catalyst/h and more preferably 0.1 kg of reaction products obtained in step (i)/kg of catalyst/h—1.5 kg of reaction products obtained in step (i)/kg of catalyst/h.

The effluent of the hydrogenation step comprises unreacted products, hydrogen, solvent, ethyleneamines and ethanolamines.

The effluent may optionally also comprise acids and/or ammonia.

Preferably ethyleneamines produced in the hydrogenation step (ii) are ethylenediamine (EDA), monoethanolamine (MEOA), diethanolamine (DEOA).

Higher ethyleneamines, such as diethylentriamine (DETA), triethylenetetramine (TETA), piperazine (PIP) and aminoethylethanolamine (AEEA) may also be formed in smaller quantities.

The effluent of the hydrogenation step may be subjected to one or more work-up steps, such as hydrogen removal, ammonia removal solvent removal and distillation to obtain the respective ethyleneamines and ethanolamines in purified form. The distillation may be conducted as a sequence of distillation steps using conventional distillation columns or divided wall columns. The destillative work-up of ethyleneamines is well-established in the state of the art and can be found in further detail in the Process Economic Program Report No. 138 "Alkyl Amines" published by SRI International, Menlo Park, California, March 1981.

If acids are present, a basic substance may be added to the effluent prior to distillation in an amount sufficient to convert the acids into a high boiling salt.

The advantages of the present invention are that it has been possible to develop a process for converting glycolaldehyde which enables a high conversion of glycolaldehyde and the formation of products, especially of MEOA, DEOA and/or EDA, in high yield and selectivity. In addition, the formation of the undesired piperazine by-product is reduced. Moreover, the conversion products are obtained in a high purity. These aims have been achieved under the premise that if glycolaldehyde is first converted with ammonia into useful intermediates, such as the triazinane derivative of formula (I) or the diamino dioxane derivative of formula (IV). Apparently, these intermediates constitute a stabilized form of glycolaldehyde and show a reduced tendency to participate in undesired side reactions, such as oligomerization or polymerization. The intermediates can be hydrogenated in a second step in the presence of hydrogen and a hydrogenation catalyst to provide the desired ethyleneamines and ethanolamines in high yields.

The process according to the invention is illustrated in detail with reference to the examples adduced below.

EXAMPLES

Example 1: Conversion of Glycolaldehyde and Ammonia in the Gas Phase (Step (i))

Gaseous glycolaldehyde was provided by evaporation of an aqueous solution of the glycolaldehyde dimer in THF (7.5 wt.-% glycolaldehyde dimer, 11.5 wt.-% THF, 80 wt.-% water and 1 wt.-% tetraglyme) by heating the solution to 160° C. in a tube evaporator comprising Raschig-rings. The gaseous feed was fed into an unheated reaction chamber operated at ambient pressure.

Gaseous ammonia at room temperature was also fed to the reaction chamber through a separate inlet.

It was observed that colorless crystals desublimated at the cooler parts of the reaction chamber.

The crystals were analyzed by gas chromatography and yielded a distinct peak. The $^{1}H$-NMR (see FIG. 1) and $^{13}C$-NMR (see FIG. 2) confirmed the crystals had the following structure:

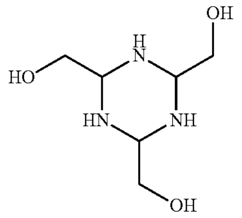

$^1H$-NMR (500 MHz, $D_2O$): 3.65 (d, 6H), 3.86 (t, 3H) ppm.

$^{13}C$-NMR (125 MHz, $D_2O$): δ4.3, 69.7 ppm.

At the cooler, bottom of the reaction chamber, a yellow-brownish clear solution condensed from the gas phase. The product solution was drawn-off from the bottom of the reaction chamber through a valve.

The product solution was analyzed with GC and yielded a distinct product peak, which was identical to the peak obtained by performing a GC on the crystals. The other substances in the product solutions were identified to be the solvents (THF, water, tetraglyme) from which the glycolaldehyde was evaporated from and excess ammonia.

The total yield of conversion products of glycolaldehyde and ammonia, including the triazinane, was about 73%.

Example 2: Hydrogenation of the Reaction Products Obtained from Example 1 (Step (ii))

35 g of the product solution obtained from Example 1 were transferred to an autoclave. The autoclave was pressurized to 20 bar and was heated to 80° C.

At 80° C., the autoclave was pressurized with hydrogen to a pressure of 100 bar.

Hydrogenation was carried out in the presence of 0.5 g of a Raney cobalt catalyst.

After a reaction time of 12 hours, the autoclave was depressurized and cooled to ambient temperature.

The composition of the product solution was analyzed by gas chromatography.

Following composition was obtained (in area percent):

EDA: 10%
MEOA: 36%
DEOA: 8%
MEG (monoethylene glycol): 3%

Example 3: Hydrogenation of the Reaction Products Obtained from Example 1 (Step (ii))

Example 3 was identical to Example 2, with the exception that an additional 10 g of ammonia was added to the autoclave at 20° C. and the solution was stirred for 1 h at 80° C. before the autoclave was pressurized to 100 bar with hydrogen gas The composition of the product solution was analyzed by gas chromatography.

Following composition was obtained (in area percent):

EDA: 6%
MEOA: 38%
DEOA: 5%
MEG (monoethylene glycol): 1%

Example 4: Conversion of Glycolaldehyde and Ammonia in the Liquid Phase (Step (i))

10 g of glycolaldehyde dimer and 11.32 g of ammonia in form of an aqueous solution of ammonia (25 wt.-%) were mixed in a reaction flask.

The reaction mixture was subjected to an evaporation step in a rotary evaporator to obtain a brownish solid residue which was isolated, washed with cold water and dried again.

Example 5: Hydrogenation of the Reaction Products Obtained from Example 4 (Step (ii))

The solid residue obtained in Example 4 was dissolved in 50 ml of methanol.

The solution was transferred into an autoclave

The autoclave was pressurized to 20 bar and was heated to 80° C.

At 80° C., the autoclave was pressurized with hydrogen to a pressure of 100 bar.

Hydrogenation was carried out in the presence of 0.5 g of a Raney cobalt catalyst.

The composition of the product solution was analyzed by gas chromatography.

Following composition was obtained (in area percent):

EDA: 4%
MEOA: 0%
DEOA: 21%
MEG (monoethylene glycol): 29%

Example 6: Hydrogenation of the Reaction Products Obtained from Example 4 (Step (ii))

Example 6 was identical to Example 5, with the exception that an additional 15 g of ammonia were added to the autoclave at 20° C. and the solution was stirred for 1 h at 80° C. before the autoclave was pressurized to 100 bar with hydrogen gas.

The composition of the product solution was analyzed by gas chromatography.

Following composition was obtained (in area percent):

EDA: 6%
MEOA: 60%
DEOA: 3%
MEG (monoethylene glycol): 0%

Example 7: Conversion of Glycolaldehyde and Ammonia in the Liquid Phase (Step (i))

Glycolaldehyde was converted with aqueous ammonia as described in Example 1 of U.S. Pat. No. 4,667,213.

A white crystalline precipitate was obtained which was washed with cold water and dried.

Example 8: Hydrogenation of the Reaction Products Obtained from Example 7 (Step (ii))

5 g of the precipitate from Example 7 were dissolved in 60 ml of methanol.

The solution was then transferred to an autoclave and was pressurized with hydrogen to a pressure of 20 bar at 20° C.

The autoclave was heated to 100° C.

At 100° C., the autoclave was pressurized with hydrogen to a pressure of 100 bar.

Hydrogenation was carried out in the presence of 1 g of a Raney cobalt catalyst.

After a reaction time of 21 hours, the autoclave was depressurized and cooled to ambient temperature.

The composition of the product solution was analyzed by gas chromatography.

Following composition was obtained (in area percent):

EDA: 0%
MEOA: 25%

DEOA: 51%

MEG (monoethylene glycol): 3%

Example 9: Hydrogenation of the Reaction Products Obtained from Example 7 (Step (ii))

Example 9 was identical to Example 8, with the exception that an additional 14 g of ammonia were added to the autoclave.

The composition of the product solution was analyzed by gas chromatography.

Following composition was obtained (in area percent):

EDA: 1%

MEOA: 76%

DEOA: 2%

MEG (monoethylene glycol): 0%

Example 10: Hydrogenation of the Reaction Products Obtained from Example 7 (Step (ii))

Example 10 was identical to Example 9, with the exception that only 2.7 g of the precipitate from Example 7 were dissolved in 60 ml of methanol and 7.6 g of ammonia were charged to the autoclave. In addition, the hydrogenation catalyst was a mixture of 0.5 g of a Raney cobalt catalyst and 1 g of a catalyst consisting of $TiO_2$.

The composition of the product solution was analyzed by gas chromatography.

Following composition was obtained (in area percent):

EDA: 0%

MEOA: 59%

DEOA: 1%

MEG (monoethylene glycol): 0%

Example 11: Hydrogenation of the Reaction Products Obtained from Example 7 (Step (ii)) in the Presence of an Acid Example 11 was identical with example 9, with the exception that 0.34 g acetic acid were additionally added to the autoclave.

The composition of the product solution was analyzed by gas chromatography.

Following composition was obtained (in area percent):

EDA: 0%

MEOA: 82%

DEOA: 6%

MEG (monoethylene glycol): 0%

The invention claimed is:

1. A process for the manufacture of ethyleneamines and ethanolamines, comprising the steps of (i) converting a glycolaldehyde derivative of formula (II)

(II)

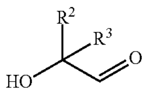

in which $R^2$, $R^3$ are—the same or different—hydrogen, alkyl, or cycloalkyl; and an aminating agent of formula (III);

$R1\text{-}NH_2$ (III)

in which $R^1$ is $C_{1-6}$-alkyl and $C_{3-6}$-cycloalkyl, in the gas or liquid phase;

(ii) feeding the reaction products obtained in step (i) into a hydrogenation reactor, where the reaction products are converted with hydrogen in the presence of a hydrogenation catalyst;

wherein the hydrogenation catalyst is a Raney copper, Raney nickel, or Raney cobalt catalyst, or a catalyst obtained from the reduction of an oxide of nickel or cobalt;

wherein prior to feeding the reaction products into step (ii), the reaction products obtained in step (i) are separated from the gas or liquid phase or the solutions or the dispersions obtained in step (i) are concentrated by evaporating at least part of the solvent comprised in such solutions.

2. A process according to claim 1, wherein the glycolaldehyde derivative of formula (II) is glycolaldehyde.

3. A process according to claim 1, wherein the molar ratio of aminating agents to glycolaldehyde derivates is in the range of 1:1 to 100:1.

4. A process according to claim 1, wherein step (i) is carried out under conditions in which hydrogenation or reductive amination of the glycolaldehyde derivative, the aminating agents and their reaction products are substantially impeded.

5. A process according to claim 1, wherein the glycolaldehyde derivative of formula (II) is provided to step (ii) in the gas or liquid form and is obtained from the hydrous thermolysis of sugars or the pyrolysis of wood.

6. A process according to claim 1, wherein the glycolaldehyde derivative of formula (II) and an aminating agent of formula (III) are provided in a gaseous form and step (i) is carried out in the gas phase.

7. A process according to claim 1, wherein step (ii) is conducted in the presence of ammonia.

8. A process according to claim 1, wherein step (ii) is conducted in the presence of one or more acids;

wherein the one or more acids is at least one of an inorganic acid or an organic acid.

9. A process according to claim 1, wherein step (i) or step (ii) is carried out in the presence of one or more solvents;

wherein the one or more solvents is at least one of water, alcohols, non-cyclic or cyclic ethers, polyalkylethers, and alkoxypolyalkylethers.

10. A process according to claim 9, wherein the one or more solvents are selected from the group consisting of water, methanol, ethanol, methyl tert-butyl ether, ethyl tert-butyl ether, dioxane, tetrahydrofuran, tetraethylene glycol dimethyl ether (tetraglyme), dipropylene glycol dimethyl ether (proglyme), bis(2-methoxyethyl) ether (diglyme) and polyethyleneoxide dimethyl ether (polyglyme).

11. A process according to claim 1, wherein the reaction products of step (i) are a triazinane derivative of formula I (I)

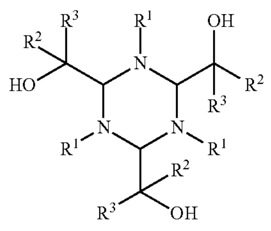

in which $R^1$, $R^2$, $R^3$ are—the same or different—hydrogen (H), alkyl, or cycloalkyl;

or a diaminodioxane derivative formula (IV)

(IV)

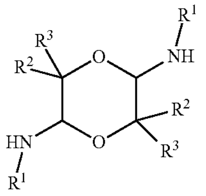

in which $R^1$, $R^2$, $R^3$ are—the same or different—hydrogen (H), alkyl, or cycloalkyl.

12. A triazinane derivative of formula I (I)

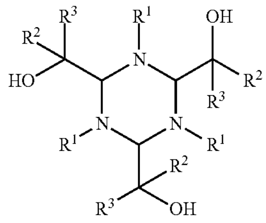

in which $R^1$, $R^2$, $R^3$ are—the same or different—hydrogen (H), alkyl, or cycloalkyl.

13. A process for the manufacture of ethyleneamines and ethanolamines by converting a triazinane derivative of formula (I):

(I)

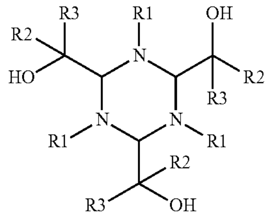

in which $R^1$, $R^2$, $R^3$ are—the same or different—hydrogen (H), alkyl, or cycloalkyl:

and/or a diaminodioxane derivative of formula (IV):

(IV)

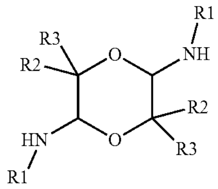

in which $R^1$, $R^2$, $R^3$ are—the same or different—hydrogen (H), alkyl;

with hydrogen in a hydrogenation reactor in the presence of a hydrogenation catalyst;

wherein the hydrogenation catalyst is a Raney copper, Raney nickel, or Raney cobalt catalyst, or a catalyst obtained from the reduction of an oxide of nickel or cobalt.

14. The process according to claim 1, wherein $R^2$, $R^3$ are—the same or different—$C_{1-6}$-alkyl, or $C_{3-6}$-cycloalkyl.

15. The process according to claim 1, wherein $R^1$ is a $C_{1-6}$-alkyl or $C_{3-6}$-cycloalkyl.

16. The process according to claim 11, wherein the reaction products of step (i) are a triazinane derivative of formula I.

17. The triazinane of claim 12, wherein $R^1$, $R^2$, $R^3$ are—the same or different—$C_{1-6}$-alkyl, or $C_{3-6}$-cycloalkyl.

18. A process for the manufacture of ethyleneamines and ethanolamines, comprising the steps of:

(i) converting a glycolaldehyde derivative of formula (II)

(II)

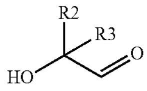

in which $R^2$, $R^3$ are—the same or different—hydrogen, alkyl, or cycloalkyl; and an aminating agent of formula (III);

$R1\text{-}NH_2$ (III)

in which $R^1$ is $C_{1-6}$-alkyl and $C_{3-6}$-cycloalkyl, in the gas or liquid phase;

(ii) feeding the reaction products obtained in step (i) into a hydrogenation reactor, where the reaction products are converted with hydrogen in the presence of a hydrogenation catalyst;

wherein the hydrogenation catalyst is a Raney copper, Raney nickel, or Raney cobalt catalyst, or a catalyst obtained from the reduction of an oxide of nickel or cobalt;

wherein prior to feeding the reaction products into step (ii), the reaction products obtained in step (i) are separated from the gas or liquid phase or the solutions or the dispersions obtained in step (i) are concentrated by evaporating at least part of the solvent comprised in such solutions (I)
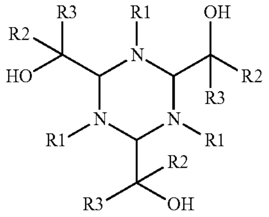
in which
$R^1$, $R^2$, $R^3$ are—the same or different—$C_{1-6}$-alkyl or $C_{3-6}$-cycloalkyl
or a diaminodioxane derivative formula (IV)
(IV)
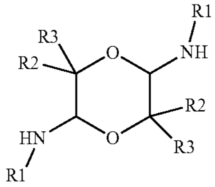
in which
$R^1$, $R^2$, $R^3$ are—the same or different $C_{1-6}$-alkyl, or $C_{3-6}$-cycloalkyl.
* * * * *